US011903763B2

(12) United States Patent
Tirumalai et al.

(10) Patent No.: US 11,903,763 B2
(45) Date of Patent: Feb. 20, 2024

(54) METHODS AND SYSTEM FOR DATA TRANSFER FOR ULTRASOUND ACQUISITION WITH MULTIPLE WIRELESS CONNECTIONS

(71) Applicant: GE Precision Healthcare LLC, Wauwatosa, WI (US)

(72) Inventors: Srihari Mukesh Tirumalai, Karnataka (IN); S M Shajedul Hasan, Rexford, NY (US); Kieran Andrew Wall, Niskayuna, NY (US); Bruno Hans Haider, Rehoboth Beach, DE (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 17/652,454

(22) Filed: Feb. 24, 2022

(65) Prior Publication Data

US 2023/0263502 A1 Aug. 24, 2023

(51) Int. Cl.
*A61B 8/00* (2006.01)
*A61B 8/08* (2006.01)

(52) U.S. Cl.
CPC .......... *A61B 8/4472* (2013.01); *A61B 8/4427* (2013.01); *A61B 8/5207* (2013.01); *A61B 8/488* (2013.01)

(58) Field of Classification Search
CPC .... A61B 8/4472; A61B 8/4427; A61B 8/5207
See application file for complete search history.

(56) References Cited

U.S. PATENT DOCUMENTS

| 7,549,961 | B1* | 6/2009 | Hwang | H04N 19/162 |
| | | | | 600/440 |
| 8,073,211 | B2 | 12/2011 | Halmann | |
| 8,824,754 | B2 | 9/2014 | Halmann | |
| 2010/0011012 | A1* | 1/2010 | Rawson | H04L 67/30 |
| | | | | 707/E17.009 |
| 2012/0057767 | A1* | 3/2012 | Halmann | A61B 8/467 |
| | | | | 382/128 |
| 2015/0363982 | A1* | 12/2015 | Kilworth | H04L 43/045 |
| | | | | 701/32.7 |
| 2016/0066893 | A1* | 3/2016 | Cho | A61B 8/4472 |
| | | | | 600/459 |

(Continued)

*Primary Examiner* — Joel Lamprecht
*Assistant Examiner* — Nyrobi Celestine
(74) *Attorney, Agent, or Firm* — McCoy Russell LLP

(57) ABSTRACT

Methods and systems are provided for ultrasound imaging. In one example, a method includes receiving ultrasound signals of a region of interest with a wireless hand-held probe assembly, generating a plurality of received digital signals based on the received ultrasound signals within the wireless hand-held probe assembly, generating each of a larger dataset and a smaller dataset from the plurality of received digital signals, transmitting the smaller dataset from the wireless hand-held probe assembly to a hub via a lower bandwidth wireless connection, transmitting the larger dataset from the wireless hand-held probe assembly to the hub via a higher bandwidth wireless connection, generating each of a low resolution image from the smaller dataset and a high resolution image from the larger dataset at the hub, and transmitting the low resolution image from the hub to a first display and the high resolution image from the hub to an electronic device.

20 Claims, 6 Drawing Sheets

(56) References Cited

U.S. PATENT DOCUMENTS

| | | | |
|---|---|---|---|
| 2016/0100824 A1* | 4/2016 | Kim | A61B 8/461 600/437 |
| 2016/0359817 A1* | 12/2016 | Mullen | H04N 21/8456 |
| 2018/0271483 A1* | 9/2018 | Nikoozadeh | A61B 8/4427 |
| 2019/0331914 A1* | 10/2019 | Lee | G06F 3/013 |
| 2020/0352546 A1* | 11/2020 | Dickie | A61B 8/4472 |
| 2021/0085290 A1* | 3/2021 | Martin | A61B 8/565 |
| 2021/0128265 A1* | 5/2021 | Jin | A61B 8/4472 |
| 2022/0142610 A1* | 5/2022 | Van Heesch | A61B 8/4236 |

\* cited by examiner

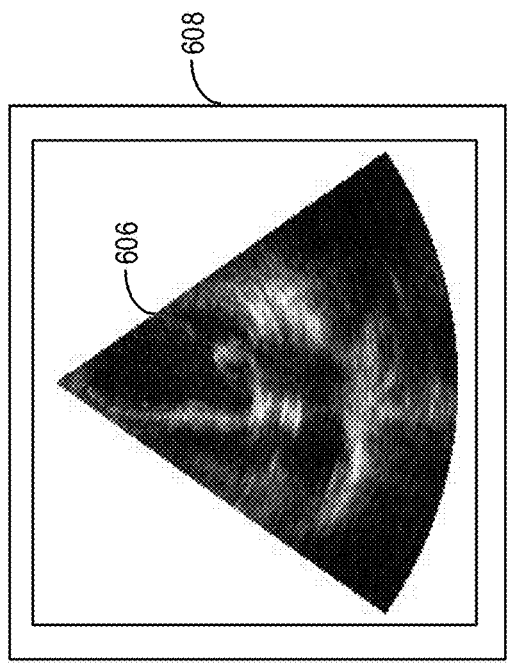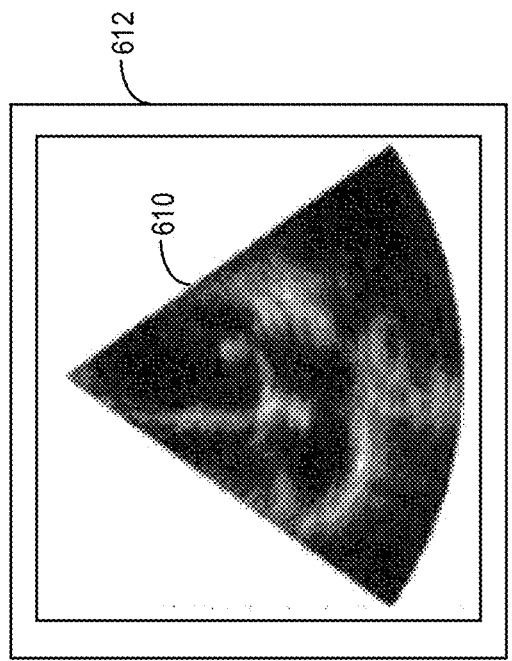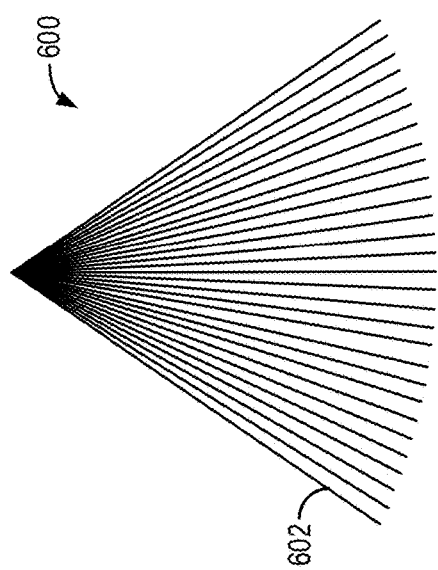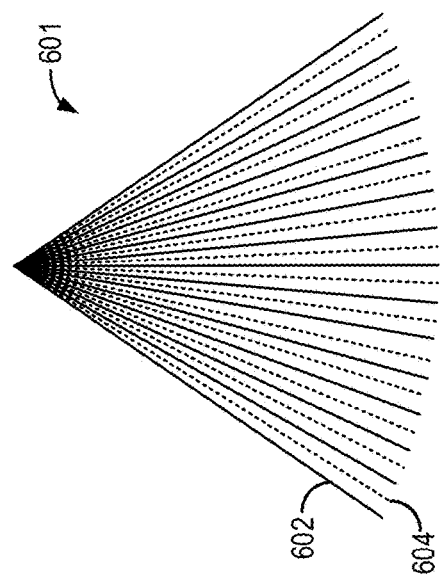
FIG. 6A
FIG. 6B

METHODS AND SYSTEM FOR DATA TRANSFER FOR ULTRASOUND ACQUISITION WITH MULTIPLE WIRELESS CONNECTIONS

TECHNICAL FIELD

Embodiments of the subject matter disclosed herein relate to ultrasound imaging, and more particularly, to wirelessly transferring data between an ultrasound probe and a computing device.

BACKGROUND

Medical ultrasound is an imaging modality that employs ultrasound waves to probe internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real-time or near real-time.

In some examples, the ultrasound probe may be a wireless probe that communicates with a hub via a wireless communications technology. For example, the hub may include electronic components for processing data received from the ultrasound probe to generate the ultrasound images. The wireless ultrasound probe may be powered by an internal rechargeable battery, for example.

BRIEF DESCRIPTION

In one aspect, a method includes receiving ultrasound signals of a region of interest with a wireless hand-held probe assembly, generating a plurality of received digital signals based on the received ultrasound signals within the wireless hand-held probe assembly, generating each of a larger dataset and a smaller dataset from the plurality of received digital signals, transmitting the smaller dataset from the wireless hand-held probe assembly to a hub via a lower bandwidth wireless connection, transmitting the larger dataset from the wireless hand-held probe assembly to the hub via a higher bandwidth wireless connection, generating each of a low resolution image from the smaller dataset and a high resolution image from the larger dataset at the hub, and transmitting the low resolution image from the hub to a first display and the high resolution image from the hub to an electronic device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings, in which:

FIGS. 6A-6B show example transmit line patterns and resulting ultrasound images, according to embodiments.

DETAILED DESCRIPTION

Embodiments of the present disclosure will now be described, by way of example, with reference to the FIGS. 1-6B, which relate to various embodiments for ultrasound imaging. Medical ultrasound imaging typically includes the placement of an ultrasound probe including one or more transducer elements onto an imaging subject, such as a patient, at the location of a target anatomical feature (e.g., abdomen, chest, etc.). During an ultrasound exam, images are acquired by the ultrasound probe and are displayed on a display device in real-time or near real-time (e.g., the images are displayed once the images are generated and without intentional delay). An operator of the ultrasound probe (e.g., an ultrasound technician) may view the images for guidance and adjust various acquisition parameters and/or the position of the ultrasound probe in order to obtain high-quality images of the target anatomical feature (e.g., the heart, the liver, the kidney, or another anatomical feature). However, the higher quality diagnostic images may include a larger amount of data than lower quality images. In the case of wireless ultrasound probes, transmitting the larger amount of data may result in higher latency. As a result, there may be a delay in the operator receiving the high-quality images, resulting in delayed adjustments to the ultrasound probe and difficulty performing the ultrasound exam. Further, acquiring and transmitting the larger amount of data may result in higher power consumption at the wireless ultrasound probe.

Figure 1:
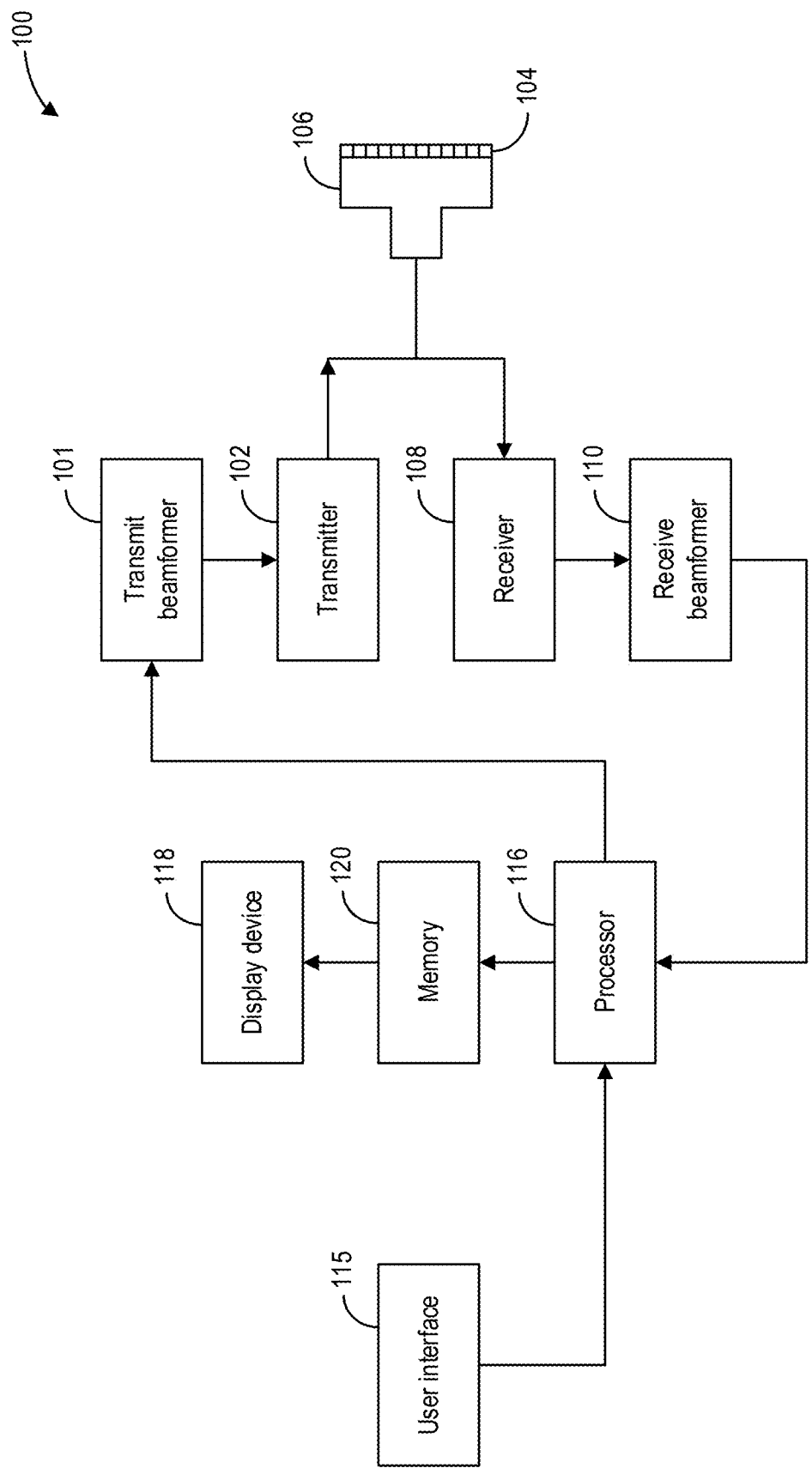
FIG. 1 shows a block diagram of an exemplary embodiment of an ultrasound system.
Figure 2:
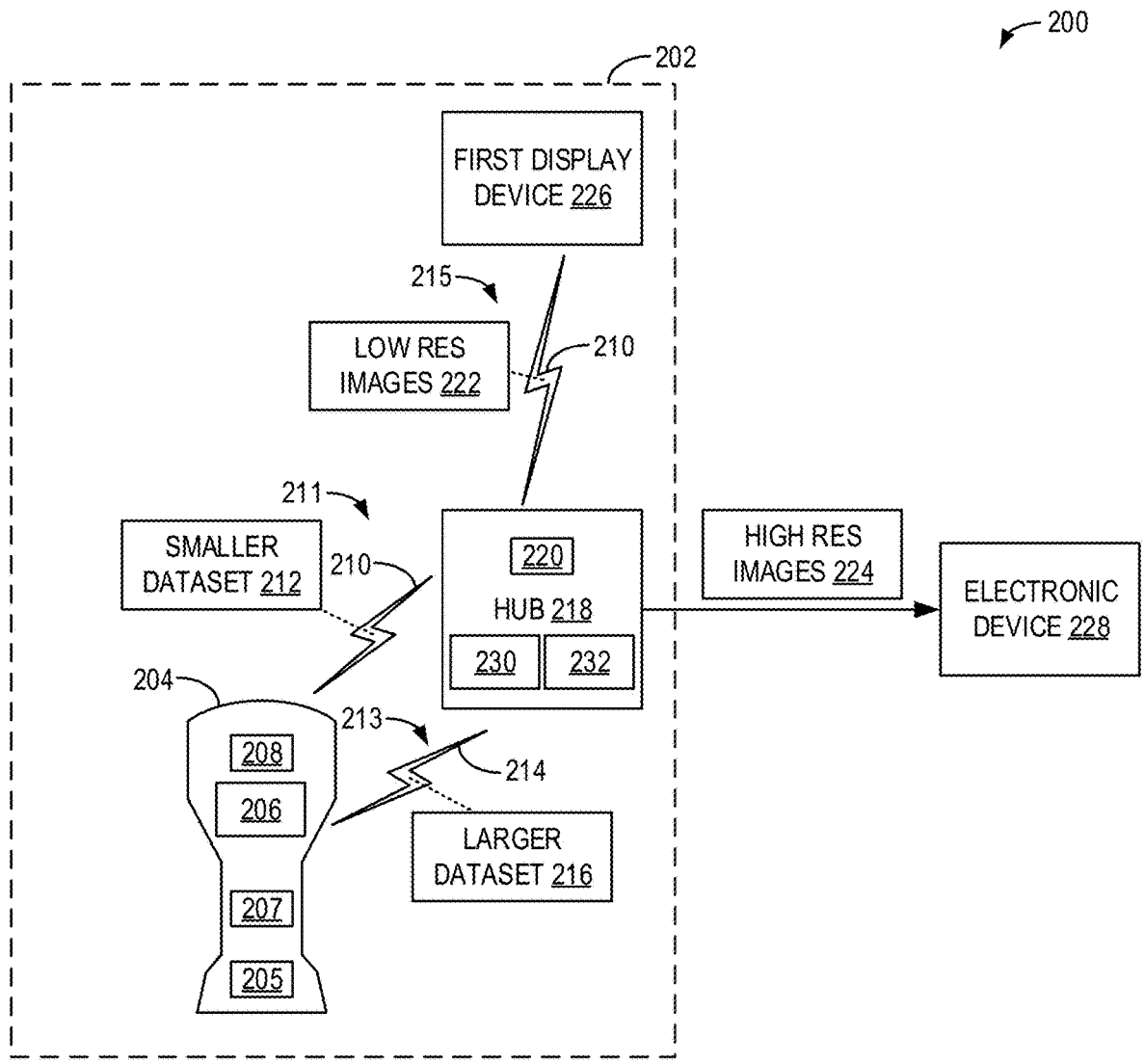
FIG. 2 is a schematic diagram illustrating a first exemplary system for generating ultrasound images via a wireless ultrasound probe, according to an exemplary embodiment.
Figure 3:
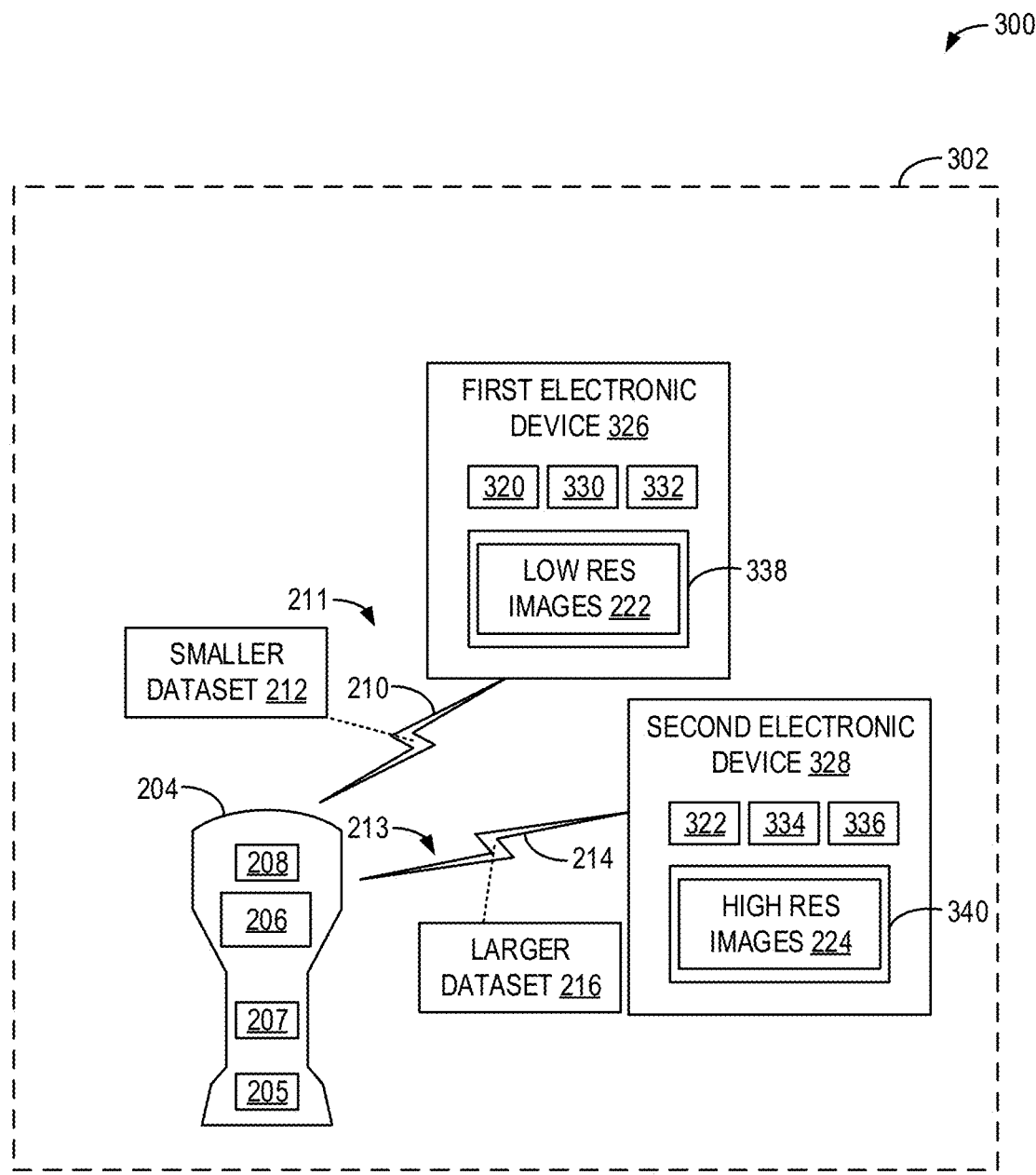
FIG. 3 is a schematic diagram illustrating a second exemplary system for generating ultrasound images via a wireless ultrasound probe, according to an exemplary embodiment

Thus, according to embodiments described herein, ultrasound data may be acquired by an ultrasound imaging system, such as the ultrasound imaging system shown in FIG. 1. The ultrasound imaging system may comprise a wireless ultrasound probe that forms a virtual network with a hub, such as schematically shown in FIG. 2. Alternatively, a hub-less network may be used, such as schematically shown in FIG. 3. The wireless ultrasound probe may utilize network slicing in order to simultaneously transfer data via two different frequency bands to the hub, such as according to the method of FIG. 4, or to two different electronic devices, such as according to the method of FIG. 5. For example, the wireless ultrasound probe may transmit a first, smaller (e.g., partial) dataset to the hub (or a first electronic device) via a first frequency band that has a higher transmission speed and a lower bandwidth and transmit a second, larger (e.g., full) dataset to the hub (or a second electronic device) via a second frequency band that has a lower transmission speed and a higher bandwidth. The smaller image dataset may be used to generate lower quality images for display to the operator in real-time, thereby providing real-time guidance to the operator. An example of the smaller image dataset and the lower quality images is shown in FIG. 6B. The larger image dataset may be used to generate higher quality images that may be used for diagnostic purposes. An example of the larger image dataset and the higher quality images is shown in FIG. 6A. Because the higher quality images may be reviewed after the ultrasound exam, the lower transmission speed may not affect ultrasound data acquisition. Further, when the higher bandwidth wireless band is unavailable, the wireless ultrasound probe may continue transmitting the partial dataset while storing the full dataset in a buffer.

Advantages that may be realized in the practice of some embodiments of the described systems and techniques are that power consumption by the probe may be reduced while exam throughput is increased. For example, a single, full dataset may be acquired by the ultrasound probe, but only a portion of the acquired data (e.g., the partial data) may be transmitted via the lower frequency band in real-time. As such, latency between data acquisition and displaying the image to the operator may be reduced. Further, transmitting the partial dataset via the lower frequency band may reduce power consumption by the probe. In this way, data may be more efficiently transmitted from the wireless ultrasound probe.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown) of a patient or subject in a region of interest. According to an embodiment, the probe 106 may be a one-dimensional transducer array probe. However, in some embodiments, the probe 106 may be a two-dimensional matrix transducer array probe. According to embodiments herein, the probe 106 may be a wireless probe, such as will be described with respect to FIG. 2. As explained further below, the transducer elements 104 may be comprised of a piezoelectric material. When a voltage is applied to a piezoelectric crystal, the crystal physically expands and contracts, emitting an ultrasonic spherical wave. As another example, the transducer elements 104 may be capacitive micromachined ultrasonic transducers (CMUTs) that transduce energy due to a change in capacitance between electrodes of the CMUTs. In this way, transducer elements 104 may convert electronic transmit signals into acoustic transmit beams.

After the elements 104 of the probe 106 emit pulsed ultrasonic signals into the body (of the patient), the pulsed ultrasonic signals are back-scattered from structures within an interior of the body, like blood cells or muscular tissue, to produce echoes of ultrasound signals that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. The ultrasound data may comprise beamformed ultrasound images, for example. Additionally, transducer element 104 may produce one or more ultrasonic pulses to form one or more transmit beams in accordance with the received echoes. The electrical signals may be also referred to herein as digital signals.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or a memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain.

The processor 116 is adapted to perform one or more processing operations according to a plurality of selectable ultrasound modalities on the data. In one example, the data may be processed in real-time during a scanning session as the echo signals are received by the receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in a live or off-line operation. Some embodiments of the invention may include multiple processors (not shown) to handle the processing tasks that are handled by the processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on the display device 118. Other embodiments may acquire and display data at different rates. For example, some embodiments may acquire data at a frame-rate of less than 10 Hz or greater than 30 Hz depending on the size of the frame and the intended application. The memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by the display device 118.

In various embodiments of the present disclosure, one or more components of ultrasound imaging system 100 may be included in a portable ultrasound imaging device. For example, as will be elaborated with respect to FIG. 2, the display device 118 and the user interface 115 may be integrated into an augmented reality (AR) device, and the processor 116 and the memory 120 may be included in a hub that is wirelessly connected to the AR device and the probe 106. For example, the display device 118 may be included in a headset of the AR device. Probe 106 may comprise a handheld probe in wireless electronic communication with the hub to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the hub, the probe, and combinations thereof.

Ultrasound images acquired by the ultrasound imaging system 100 may be further processed. In some embodiments, ultrasound images produced by ultrasound imaging system 100 may be transmitted to an image processing system, which may produce images for display at the display device 118 as well as other display devices, as will be described below.

Referring now to FIG. 2, an example wireless ultrasound imaging system 200 is shown. The wireless ultrasound imaging system 200 is one embodiment of the ultrasound imaging system 100 of FIG. 1. As such, although not explicitly shown, components of FIG. 1, such as the transmit beamformer 101, the transmitter 102, the receiver 108, and the receive beamformer 110 may also be included in the wireless ultrasound imaging system 200 and function as previously described.

The wireless ultrasound imaging system 200 includes a virtual network 202 formed between an ultrasound probe 204, a hub 218, and a first display device 226. The ultrasound probe 204 (e.g., the ultrasound probe 106 of FIG. 1) is a wireless ultrasound probe that is powered by a battery 205. The ultrasound probe 204 may also be referred to herein as a wireless hand-held probe assembly and may include some or all of the transmit beamformer 101, the transmitter 102, the receiver 108, and the receive beamformer 110 described with respect to FIG. 1 within a shared enclosure or housing. The battery 205 may be a rechargeable battery, for example, that is configured to store electrical power received from a power supply in a wired or wireless fashion. The ultrasound probe 204 further includes a processor 207 and a memory 206. The memory 206 may be configured to at least temporarily store data acquired by the ultrasound probe 204 prior to its transfer to the hub 218 via the virtual network 202, which will be elaborated below. For example, the memory 206 may comprise a buffer memory. As such, the ultrasound probe 204 may continue acquiring data even if communication between the ultrasound probe 204 and the hub 218 becomes temporarily disrupted, store the acquired data in the memory 206, and then transfer the acquired data from the memory 206 to the hub 218 once communication is re-established. Further, the memory 206 may include instructions for acquiring ultrasound image data according to different image acquisition modes (examples of which will be described herein), performing processing on the acquired ultrasound image data via the processor 207, establishing wireless connections with the hub 218, and transmitting ultrasound image data, as will be further described below. For example, instructions included in the memory 206 may be executed by the processor 207.

The ultrasound probe 204 further includes a wireless transceiver 208. The wireless transceiver 208 may comprise one or more transceivers that enable the ultrasound probe 204 to transmit and receive data over multiple wireless communication links, including a plurality of frequency bands. Similarly, the hub 218 comprises a wireless transceiver 220 that enables data transmission between the hub 218 and the ultrasound probe 204 over the plurality of frequency bands. The hub 218 may further comprise, or be in electronic communication with, a processor 230 and a memory 232. For example, the hub 218 may comprise an image processing system. The processor 230 includes one or more processors that are located within the hub 218 or remotely accessed via the hub 218. For example, the processor 230 may include a beamforming engine (e.g., the receive beamformer 110 of FIG. 1) that receives raw or partially processed ultrasound image data from the ultrasound probe 204 and generates ultrasound images from the raw or partially processed ultrasound image data. Similarly, the memory 232 may be located within the hub 218 or remotely accessed via the hub 218 and may store raw ultrasound image data, processed or partially processed ultrasound image data, ultrasound images, instructions for acquiring the ultrasound image data, instructions for processing the ultrasound images, and so forth.

The virtual network 202 utilizes network slicing and includes a first frequency band 210 and a second frequency band 214. The first frequency band 210 is a lower frequency band (e.g., 7 gigahertz, GHz, or less) having a larger data transmission range (e.g., distance), and the second frequency band is a higher frequency band (e.g., 60 GHz or millimeter wave, such as 5G) having a smaller data transmission range compared with the lower frequency band. The first frequency band 210 is a lower latency, lower bandwidth frequency, whereas the second frequency band 214 is a higher latency, higher bandwidth frequency. Thus, the first frequency band 210 enables a faster transfer of a smaller amount of data, and the second frequency band 214 enables a slower transfer of a larger amount of data.

A first wireless connection 211 is established between the ultrasound probe 204 and the hub 218 over the first frequency band 210, and a second wireless connection 213 is established between the ultrasound probe 204 and the hub 218 over the second frequency band 214. The second frequency band 214 may utilize a direct line-of-sight for establishing and maintaining the second wireless connection 213. For example, waves of the second frequency band 214 may be unable to penetrate certain structures that may be placed between the transceiver 208 of the ultrasound probe 204 and the transceiver 220 of the hub 218. In contrast, the first frequency band 210 may not utilize line-of-sight for establishing and maintaining the first wireless connection 211. As such, connectivity disruptions may occur more frequently in the second wireless connection 213 relative to the first wireless connection 211.

Further, a third wireless connection 215 is established between the hub 218 and the first display device 226 over the first frequency band 210. The hub 218 receives a first, smaller dataset 212 of ultrasound image data acquired by the ultrasound probe 204 via the first wireless connection 211 (e.g., via the first frequency band 210) and receives a second, larger dataset 216 of the ultrasound image data acquired by the ultrasound probe 204 via the second wireless connection 213 (e.g., via the second frequency band 214). The smaller dataset 212 may include a subset of transmit lines, for example, while the larger dataset 216 may include all of the transmit lines acquired during a scan, such as illustrated in FIGS. 6A and 6B and described below. As such, the smaller dataset 312 may include a portion (e.g., subset) of the data in the larger dataset 216 and may be also referred to herein as a partial dataset. The larger dataset 216 may be also referred to herein as a full dataset. The full dataset may comprise substantially all of the data acquired by the ultrasound probe 204 during a scan or less than all of the data acquired by the ultrasound probe 204 during the scan.

The processor 207 of the ultrasound probe 204 may select which data of the larger dataset 216 to include in the smaller dataset 212 based on instructions in the memory 206, at least in some examples. For example, the processor 207 may select data according to a bandwidth of the first frequency band 210 in order to send a highest amount of data over the first wireless connection 211. Thus, the instructions may include instructions for skipping lines, trimming a field of view, or so forth in a hierarchical format that balances reducing data size with preserving image quality.

The hub 218 processes the smaller dataset 212 (e.g., via the processor 230) to produce low resolution images 222, which are transmitted to the first display device 226 via the third wireless connection 215 (e.g., via the first frequency band 210). Due to the lower latency of the first frequency band 210 and the increased connection stability of the first wireless connection 211, the smaller dataset 212 and the low resolution images 222 may be transmitted in substantially real-time. For example, the hub 218 may receive the smaller dataset 212 from the ultrasound probe 204 substantially instantaneously as it is sent over the first frequency band 210 and the first wireless connection 211. The hub 218 may process the smaller dataset 212 in real-time, as it is received, and transmit the low resolution images 222 to the first display device 226 in real-time. The first display device 226 may receive the low resolution images 222 substantially instantaneously as they are sent from the hub 218 via the first frequency band 210 and the third wireless connection 215.

The hub 218 is also communicatively coupled to an electronic device 228 via a wired or wireless connection (e.g., via the second frequency band 214). The hub 218 processes the larger dataset 216 to produce high resolution images 224, which are further communicated to the electronic device 228. The second frequency band 214 has higher latency but also higher bandwidth (e.g., compared with the first frequency band 210), enabling larger amount of data to be transferred, but with greater delay than the first frequency band 210. Further, the second wireless connection 213 may be more prone to connection disruptions, as mentioned above. Thus, in some embodiments, the larger dataset 216 may be transmitted to the hub 218 from the ultrasound probe 204 over the second frequency band 214 and the second wireless connection 213 in at a rate that is slower than real-time. In some examples, the transfer of the larger dataset 216 from the ultrasound probe 204 may be delayed by seconds, minutes, hours, or more. Once the hub 218 receives the larger dataset 216, the hub 218 may process the larger dataset 216 to produce the high resolution images 224 without intentional delay or at a later time, such as in response to a request to process the larger dataset 216 from a user. Further, once generated, the high resolution images 224 may be transferred from the hub 218 to the electronic device 228 without intentional delay or at a later time (e.g., in response to a request to display the high resolution images 224 from the user).

The electronic device 228 may include one or more of a computing device, a picture archiving and communications system, and a second display device. The first display device 226 is a display device used by a technician operating the ultrasound probe 204, whereas the electronic device 228 may be remotely located or local to the ultrasound probe 204. For example, the second display device may be a display device of a diagnosing clinician that is remote from the ultrasound exam (e.g., located in a different room or a different facility). For example, the diagnosing clinician may review the high resolution images 224 after the ultrasound exam to make a diagnosis. The first display device 226 may be a headset of an AR device worn by the technician, such as described above. Alternatively, the first display device 226 may be another type of device that is local to the technician, such as a computer monitor, a touchscreen, or the like. The second display device of the electronic device 228 may utilize virtually any type of display technology. For example, the electronic device 228 may be a desktop computer, laptop computer, a tablet computer, or a smartphone and may utilize an external monitor, a built-in display, a touchscreen, and/or a projector for displaying the high resolution images 224. Thus, the low resolution images 222 may be displayed to the technician in real-time to provide guidance images to the technician for probe operation, whereas the high resolution images 224 may provide diagnostic images that may be displayed to the clinician at a delay compared with the low resolution images 222. In this way, the network slicing of the virtual network 202 may enable high quality ultrasound images to be obtained via the ultrasound probe 204 without delaying real-time visual guidance provided to the technician operating the ultrasound probe 204.

It should be understood that the wireless ultrasound imaging system 200 shown in FIG. 2 is an illustrative example of one embodiment of a wireless ultrasound imaging system that utilizes network slicing to transfer different datasets, including portions of a dataset, over different frequency bands. Another appropriate wireless ultrasound imaging system may include more, fewer, or different components without departing from the scope of this disclosure.

For example, turning to FIG. 3, a wireless ultrasound imaging system 300 is shown. The wireless ultrasound imaging system 300 is similar to the wireless ultrasound imaging system 200 of FIG. 2 except that the wireless ultrasound imaging system 300 a hub-less system. As such, components of FIG. 3 previously introduced in FIG. 2 that are numbered the same function as previously described and may not be reintroduced.

The wireless ultrasound imaging system 300 includes a virtual network 302 that is similar to the virtual network 202 of FIG. 2. For example, the virtual network 302 uses network slicing to connect the ultrasound probe 204 to a first electronic device 326 via the first wireless connection 211 and the first frequency band 210 and to a second electronic device 328 via the second wireless connection 213 and the second frequency band 214. Thus, instead of both the smaller dataset 212 and the larger dataset 216 being sent to a single electronic device (e.g., the hub 218 of FIG. 2), the smaller dataset 212 and the larger dataset 216 are separately sent directly to different electronic devices for further processing and/or display.

In the embodiment shown, the first electronic device comprises a wireless transceiver 320, a processor 330, and a memory 332. For example, the wireless transceiver 320 may enable the first electronic device 326 to receive the smaller dataset 212 from the ultrasound probe 204 via the first, smaller bandwidth wireless connection 211, and the processor 330 may further process the smaller dataset 212 based on instructions stored in the memory 332 to generate and display the low resolution images 222. The first electronic device 326 may further include, or may be communicatively coupled to, a first display device 338, which may display the low resolution images 222 in real-time, as the ultrasound signals in the smaller dataset 212 are acquired. For example, the first electronic device 326 may be a portable computing device, such as a personal digital assistant, a tablet, a laptop computer, an AR headset, a smartphone, and the like. Thus, the first display device 338 may be integral to the first electronic device 326 that receives the smaller dataset 212 from the ultrasound probe 204. Further, the first electronic device 326 may be local to the ultrasound probe 204 so that the first display device 338 is visible to the operator of the ultrasound probe 204.

Similarly, in the embodiment shown, the second electronic device 328 comprises a wireless transceiver 322, a processor 334, and a memory 336. The wireless transceiver 322 may enable the second electronic device 328 to receive the larger dataset 216 from the ultrasound probe 204 via the second, larger bandwidth wireless connection 213. The processor 334 may further process the larger dataset 216 based on instructions stored in the memory 336 to generate, display, and/or save the high resolution images 224 (e.g., to the memory 336). In some embodiments, the second electronic device 328 may include, or may be communicatively coupled to, a second display device 340. The high resolution images 224 may be output to the second display device 340 in response to receiving a user request to view the high resolution images 224, for example. As one example, the second electronic device 328 may comprise a picture archiving and communications system. Additionally or alternatively, the second electronic device 328 may comprise a computing device, such as personal digital assistant, a tablet, a laptop computer, a desktop computer, a smartphone, and a distributed computing system. Further, in some embodiments, at least a portion of the second electronic device 328 may be located remotely from the ultrasound probe 204.

Further, it may be understood that at least one of the wireless transceiver 322, the processor, the memory, and the second display device 340 may be located in a separate housing and/or location and not in a shared enclosure. For example, the components described with respect to the second electronic device 328 may be distributed throughout a plurality of devices. As an example, the larger dataset 216 may be received by the wireless transceiver 322, which may be included in an access point that is further electronically connected to the processor 334 and/or the memory 336 via wireless or wired communications technologies.

Figure 4:
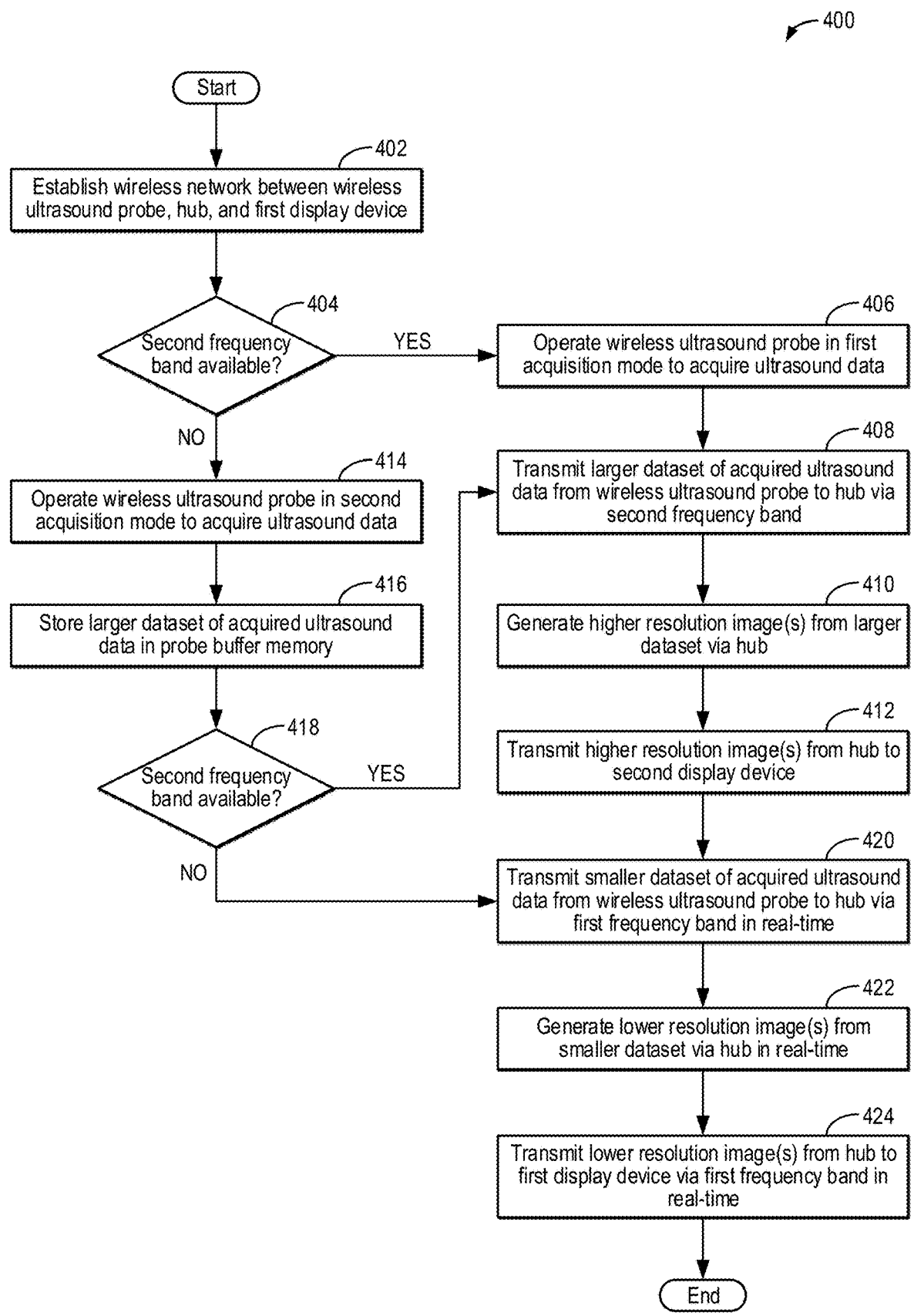
FIG. 4 is a flow chart illustrating a first example method for performing ultrasound imaging with a wireless hand-held probe, according to an exemplary embodiment.

FIG. 4 shows a flow chart illustrating an example method 400 for transferring ultrasound image data over a virtual network during an ultrasound exam. The method 400 is described with regard to the systems and components of FIGS. 1 and 2, though it may be appreciated that the method 400 may be implemented with other systems and components without departing from the scope of the present disclosure. The method 400 may be carried out by one or more processors (e.g., the processor 207 and the processor 230 of FIG. 2) according to instructions stored in at least one non-transitory memory, such as the memory 232 of the hub 218 and/or the memory 206 of the ultrasound probe 204 of FIG. 2. For example, a processor of a wireless ultrasound probe and a processor of a hub (e.g., an image processing hub) may execute the method 400 in combination.

At 402, the method 400 includes establishing a wireless network between the wireless ultrasound probe, the hub, and a first display device. The wireless network may comprise a first frequency band (e.g., the first frequency band 210 of FIG. 2) that has a lower bandwidth and a second frequency band (e.g., the second frequency band 214 of FIG. 2) that has a higher bandwidth. Thus, the wireless network may be a multi-frequency wireless network that uses network slicing. The first frequency band may transmit data farther and at a lower latency than the second frequency band. As an example, the first frequency band may be 7 Ghz or less, whereas the second frequency band may be at least 60 GHz or millimeter wave technology (e.g., 5G). Thus, the first frequency band may be a lower frequency band, and the second frequency band may be a higher frequency band. The wireless ultrasound probe (e.g., the ultrasound probe 204 of FIG. 2) may be configured to connect to the hub (e.g., the hub 218 of FIG. 2) via both the first frequency band and the second frequency band, and the hub may be further configured to connect to the first display device via the first frequency band (and not the second frequency band). The first display device (e.g., first display device 226 of FIG. 2) is local to the wireless ultrasound probe (e.g., in a same room) and comprises a display for a technician performing the ultrasound exam. As mentioned above with respect to FIGS. 1 and 2, the first display device may be included in an augmented reality headset worn by the technician, however other types of display devices are also possible. Thus, establishing the wireless network may include establishing a first, lower bandwidth wireless connection between the wireless ultrasound probe and the hub via the first frequency band, establishing a second, higher bandwidth wireless connection between the wireless ultrasound probe and the hub via the second frequency band, and establishing a third wireless connection between the hub and the first display device via the first frequency band.

The ultrasound exam may be performed responsive to establishing the connections between the wireless ultrasound probe, the hub, and the first display device via the first frequency band. For example, the connections over the first frequency band may be established responsive to commencing the ultrasound exam, such as in response to an ultrasound exam protocol being selected or receiving another type of user input to commence the ultrasound exam. Additionally or alternatively, the first wireless and the third wireless connection may be established in response to acquiring data via the wireless ultrasound probe. For example, the wireless ultrasound probe may automatically establish the wireless connections over the first frequency band in response to sending and/or receiving ultrasound signals. Because a data transmission range is lower for the second frequency band and the second frequency band may utilize direct line-of-sight for the connection, there may be situations where the wireless ultrasound probe becomes at least temporarily disconnected from the hub via the second wireless connection. For example, the wireless ultrasound probe may at least temporarily lose line-of-sight with the hub during the ultrasound exam. In some embodiments, operation of the wireless ultrasound probe may be adjusted in response to the second frequency band being unavailable for establishing the second wireless connection in order to reduce power consumption by the wireless ultrasound probe.

Therefore, at 404, the method 400 includes determining if the second frequency band is available. For example, the wireless ultrasound probe may attempt to establish the second wireless connection with the hub (or vice versa) over the second frequency band and may determine that the second frequency band is unavailable in response to the second wireless connection not being established within a pre-determined, non-zero threshold duration. Additionally or alternatively, the wireless ultrasound probe may repeatedly attempt to establish the second wireless connection to the hub and determine that the second frequency band is unavailable in response to reaching a pre-determined, non-zero threshold number of consecutive attempts without establishing the second wireless connection.

Additionally or alternatively, in some embodiments, the second frequency band may be selectively available. For example, the technician may input a request to establish the second wireless connection, and the second frequency band may become available in response to receiving the request. The request may comprise a "freeze" or "store" request, for example, and may be received via a user interface (e.g., the user interface 115 of FIG. 1). In such examples, the second wireless connection may not be established until the request is received. Similarly, the technician may input a second, different request to disconnect the wireless ultrasound probe from the hub via the second connection, and the second frequency band may become unavailable in response to receiving the second request. As another example, the first request may time out after a pre-determined duration or pre-determined amount of data transfer via the second wireless connection.

If the second frequency band is available (e.g., there is an active connection between the wireless ultrasound probe and the hub via the second frequency band), the method 400 proceeds to 406 and includes operating the wireless ultrasound probe in a first acquisition mode to acquire ultrasound data. The first acquisition mode, used when both the first wireless connection and the second wireless connection are established between the wireless ultrasound probe and the hub, may be a higher power consumption mode compared with a second acquisition mode that may be used when the second frequency band is not available, as will be described below at 414. Thus, power may be consumed from a battery of the wireless ultrasound probe at a faster rate while operating in the first acquisition mode than while operating in the second acquisition mode. Operating the wireless ultrasound probe in the first acquisition mode may include acquiring more transmit lines, acquiring data at a higher pulse repetition frequency, acquiring data at a higher frame rate, acquiring data from a larger region of interest (ROI), and/or performing more data processing on the acquired ultrasound data via the processor of the probe than when the wireless ultrasound probe is operated in the second acquisition mode. As such, operating in the first acquisition mode may include performing a more comprehensive or detailed acquisition at the wireless ultrasound probe. Further, it may be understood that both operating in the first acquisition mode and operating in the second acquisition mode includes receiving ultrasound signals of the ROI with the wireless ultrasound probe, generating a plurality of received digital signals based on the received ultrasound signals within the wireless ultrasound probe, and generating each of a larger dataset and a smaller dataset from the plurality of received digital signals.

At 408, the method 400 includes transmitting the larger dataset of the acquired ultrasound data from the wireless ultrasound probe to the hub via the second frequency band. The larger dataset may include substantially all of the data acquired during the ultrasound exam, including a larger field of view and every transmit line acquired, at least in some embodiments. Alternatively, the larger dataset may include less than all of the data acquired while operating Further, the larger dataset may undergo additional processing at the wireless ultrasound probe and error correction in the wireless channel compared with a smaller dataset that will be further described below (e.g., at 420). The error correction in the wireless channel (e.g., the second wireless connection) may ensure that the larger dataset is transmitted without errors but may reduce the transmission speed. For example, transmission with error correction may result in slower transmission speeds than transmission without error correction.

As explained above with respect to FIG. 2, the data transmitted via the second frequency band may not be used to generate real-time images displayed to the operator during the ultrasound exam. Therefore, transmitting the larger dataset of the acquired ultrasound data from the wireless ultrasound probe to the hub via the second frequency band may include transmitting the larger dataset to the hub at a rate that is slower than real-time (e.g., slower than an image data acquisition rate), at least in some examples. Further, if the second frequency band does not have sufficient bandwidth to transfer all of the available data in the larger dataset, remaining data that has not been transferred may be queued in a buffer memory of the probe (e.g., the memory 206 of FIG. 2) and transferred via the second frequency band as bandwidth becomes available.

At 410, the method 400 includes generating higher resolution image(s) from the larger dataset via the hub. For example, the processor may process ultrasound signals in the larger dataset to generate slices or frames of ultrasound information (e.g., ultrasound images). In one example, generating the higher resolution image(s) may include determining an intensity value for each pixel to be displayed based on the received image data (e.g., 2D or 3D ultrasound data). Because the larger dataset includes more image data compared with the smaller dataset, more information is available for generating pixels of the resulting image. For example, the higher resolution images may have more pixels per inch than lower resolution image(s) that may be generated from the smaller dataset (e.g., at 422), as further described below. Because of the increased detail in the higher resolution images, the higher resolution images may comprise diagnostic-quality images.

In some examples, the higher resolution image(s) may be generated at a rate that is slower than real-time, which may be also referred to herein as less than real-time. As one example, the higher resolution image(s) may be generated during the ultrasound exam but at a frame rate that is less than the frame rate of the ultrasound data acquisition. As another example, at least a portion of the higher resolution image(s) may be generated after all of the data is acquired for the ultrasound exam. In still another example, some or all of the higher resolution image(s) may be generated in response to receiving a user request for diagnostic images.

At 412, the method 400 includes transmitting the higher resolution image(s) from the hub to a second display device. The second display device may be a display device of a diagnosing clinician, for example. In some embodiments, the second display device may be remote from the wireless ultrasound probe. For example, the second display device may be located in a different room than the wireless ultrasound probe and/or a different room from the hub. Further, as discussed above with respect to FIG. 2, the higher resolution images may be transmitted to the second display device not in real-time, at least in some examples. Once transmitted to the second display device, the higher resolution image(s) may be displayed on the second display device. As one example, the diagnosing clinician may select one or more of the high resolution image(s) for display at the second display device via the user interface.

At 420, the method 400 includes transmitting the smaller dataset of the acquired ultrasound data from the wireless ultrasound probe to the hub via the first frequency band in real-time. The smaller dataset comprises a subset of the larger dataset. For example, the smaller dataset may include a portion of the transmit lines, a trimmed field of view, and/or a portion of the acquired frames. For example, the smaller dataset may include every other transmit line, such as illustrated in FIGS. 6A and 6B and described below. Further, a reduced amount of pre-processing may be performed on the smaller dataset at the probe. In some examples, an amount of data in the smaller dataset may be capped based on a known bandwidth of the first frequency band so that the known bandwidth is not exceeded. The smaller dataset may be transmitted from the probe to the hub via the first wireless connection in real-time, as the ultrasound data is acquired. Further, error correction may not be performed during the transmission of the smaller dataset via the first frequency band in order to increase transmission speeds, at least in some embodiments.

At 422, the method 400 includes generating the lower resolution image(s) from the smaller dataset via the hub in real-time. The lower resolution image(s) may be generated in a similar manner to that described above at 410 for the higher resolution images. However, because less image information is contained in the smaller dataset compared to the larger dataset, the lower resolution images may have fewer pixels per inch, resulting in less image detail. Further, the lower image resolution image(s) may be generated in real-time, substantially at the time of data acquisition and transmission to the hub.

At 424, the method 400 includes transmitting the lower resolution image(s) from the hub to the first display device via the first frequency band in real-time. For example, transmitting the lower resolution image(s) to the first display device may include transmitting each lower resolution image to the first display device as it is generated. The method 400 may then end. In this way, the lower resolution images(s) may be displayed to the operator in real-time via data transfer using the faster but smaller capacity first frequency band. As a result, real-time guidance feedback may be provided for the ultrasound exam that may not include sufficient detail for making a diagnosis. Further, by transferring the larger dataset via the slower but larger capacity second frequency band, higher resolution image(s) may be generated and displayed to the diagnosing clinician without delaying the real-time feedback provided to the operator during the ultrasound exam.

Returning to 404, if the second frequency band is not available (e.g., there is not an active connection between the wireless ultrasound probe and the hub via the second frequency band), the method 400 proceeds to 414 and includes operating the wireless ultrasound probe in a second acquisition mode to acquire the ultrasound data. The second acquisition mode used when the second frequency band is unavailable may be a lower power consumption mode compared with the first acquisition mode described above at 406. Operating the wireless ultrasound probe in the second acquisition mode may include acquiring fewer transmit lines, acquiring data at a lower pulse repetition frequency, acquiring data at a lower frame rate, acquiring data from a smaller ROI, and/or performing less data processing on the acquired ultrasound data at the probe than when the wireless ultrasound probe is operated in the first acquisition mode. As such, operating in the second acquisition mode may include performing a less comprehensive or detailed acquisition at the wireless ultrasound probe. In some embodiments, there may be differences in the second acquisition mode depending on a type of ultrasound exam being performed. For example, cardiac ultrasound imaging may prioritize the pulse repetition frequency, whereas abdominal ultrasound imaging may prioritize resolution. Thus, as an example, the pulse repetition frequency may be higher while operating in the second acquisition mode when cardiac ultrasound imaging is performed compared to when abdominal ultrasound imaging is performed.

In some embodiments, an amount and quality of data acquired by the wireless ultrasound probe in the second acquisition mode may be unchanged from the first acquisition mode. However, by performing less data processing at the probe, the power consumption may be reduced. In other embodiments, the amount and quality of data acquired by the wireless ultrasound probe may be reduced while operating in the second acquisition mode, but the amount and quality of the data acquired may be such that a diagnostic quality (e.g., high resolution) image may be generated from the larger dataset. As such, the larger dataset may be similar to or the same as the ultrasound data acquired while operating in the first acquisition mode, at least in some embodiments.

Further, in some embodiments, operating in the second acquisition mode may include outputting a notification to the operator, such as via the first display device. The notification may state that the wireless ultrasound probe is not connected to the hub via the second frequency band, for example. Additionally or alternatively, the notification may include a visual icon or audible alert (e.g., a chime) that is associated with the disconnection of the second frequency band. As such, the operator may be given the opportunity to correct the connectivity issue, if desired.

At 416, the method 400 includes storing the larger dataset of the acquired ultrasound data in the probe buffer memory. Because the second frequency band is unavailable and the first frequency band may not have the bandwidth to transmit the larger dataset from the wireless ultrasound probe to the hub, the larger dataset is stored locally on the probe until the second frequency band becomes available. Further, by reducing the processing of the acquired ultrasound data at the probe, more probe memory may be available to store the larger dataset.

Additionally, in some embodiments, operating in the second acquisition mode may include erasing the larger dataset from the probe memory after a pre-determined non-zero duration of time has elapsed (e.g., minutes or hours), in response to the operator selecting subsequent images or videos, and/or in response to the ultrasound exam ending. In this way, the probe memory may not serve as a long-term storage for the larger dataset, but may be used to temporarily store the larger dataset when the second frequency band is unavailable for transferring the larger dataset.

At 418, the method 400 includes again determining if the second frequency band is available, such as described above at 404. If the second frequency band remains unavailable, the method 400 may proceed to 420 to transmit the smaller dataset of the acquired ultrasound data from the wireless ultrasound probe to the hub via the first frequency band in real-time, such as described above. The larger dataset may thus remain stored in the buffer memory of the probe. In response to the second frequency band becoming available, the method 400 proceeds to 408 to transmit the larger dataset of the acquired ultrasound data, including the data stored in the probe memory to the hub. Thus, operating in the second acquisition mode may include transmitting the larger dataset to the hub in response to the second frequency band becoming available. In some embodiments, the wireless ultrasound probe may be adjusted to operating in the first acquisition mode in response to the second frequency band becoming available. It may be understood that if the second frequency band becomes unavailable at any point while operating in the first acquisition mode, the wireless ultrasound probe may be transitioned to operating in the second acquisition mode.

Figure 5:
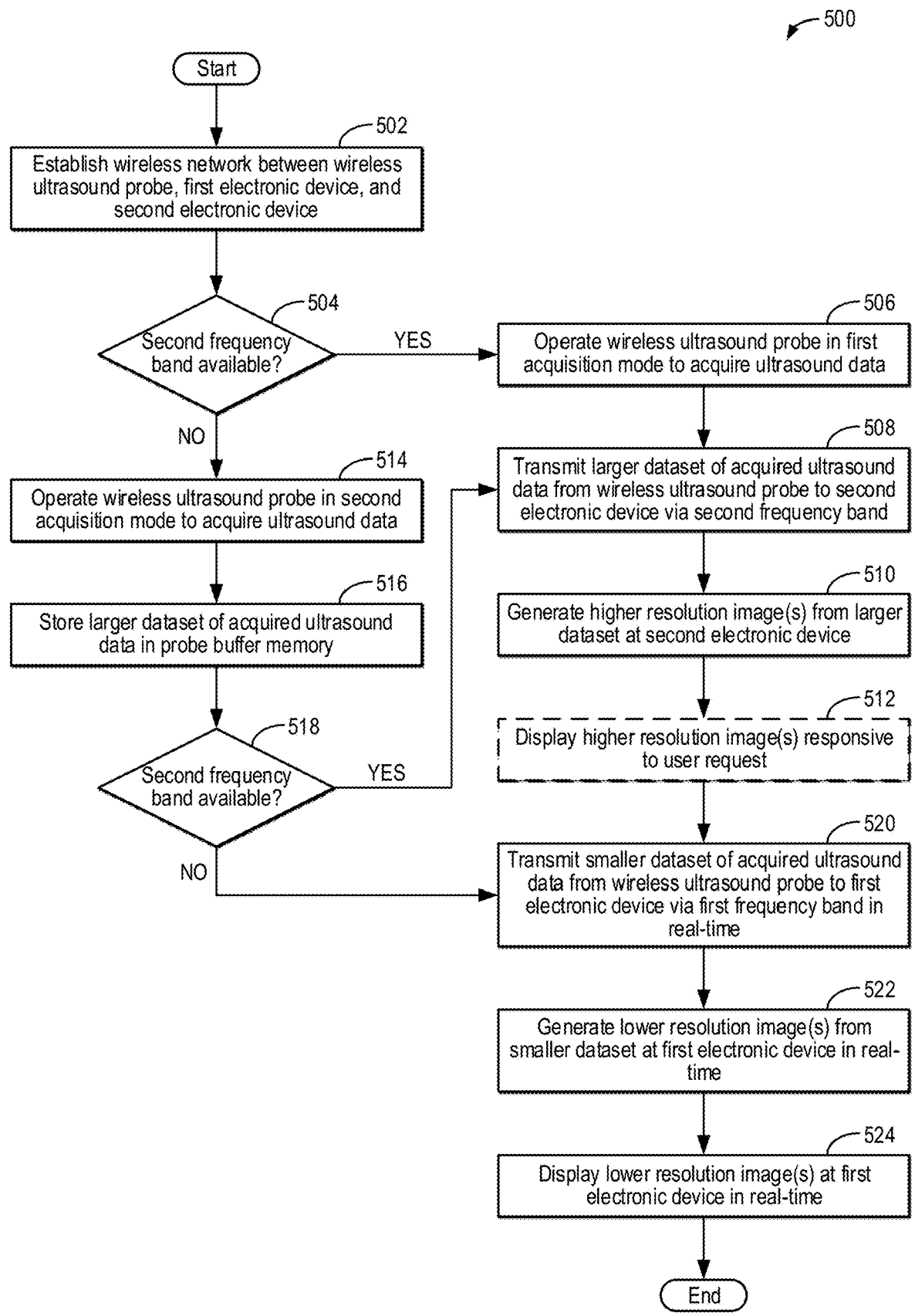
FIG. 5 is a flow chart illustrating a second example method for performing ultrasound imaging with a wireless hand-held probe, according to an exemplary embodiment.

FIG. 5 shows a flow chart illustrating an example method 500 for transferring ultrasound image data over a virtual network during an ultrasound exam via a hub-less system. The method 500 is described with regard to the systems and components of FIGS. 1 and 3, though it may be appreciated that the method 500 may be implemented with other systems and components without departing from the scope of the present disclosure. The method 500 may be carried out by one or more processors (e.g., the processor 207, the processor 330, and/or the processor 334 of FIG. 3) according to instructions stored in at least one non-transitory memory, such as the memory 332 of the first electronic device, the memory 336 of the second electronic device, and/or the memory 206 of the ultrasound probe 204 of FIG. 3. For example, a first portion of the method 500 may be executed by the ultrasound probe 204, a second portion of the method 500 may be executed by the first electronic device 326, and a third portion of the method 500 may be executed by the second electronic device 328 such that the method 500 is executed in combination. Further, the method 500 is similar to the method 400 of FIG. 4. Thus, differences between the two methods will be highlighted below for the sake of brevity At 502, the method 500 includes establishing a wireless network between the wireless ultrasound probe, a first electronic device, and a second electronic device. The wireless network may comprise a first frequency band (e.g., the first frequency band 210 of FIG. 2) that has a lower bandwidth and a second frequency band (e.g., the second frequency band 214 of FIG. 2), such as described above at 402. The wireless ultrasound probe (e.g., the ultrasound probe 204 of FIG. 2) may be configured to connect to the first electronic device (e.g., the first electronic device 326 of FIG. 3) via the first frequency band and to the second electronic device (e.g., the second electronic device 328 of FIG. 3) via the second frequency band. The first electronic device is local to the wireless ultrasound probe (e.g., in a same room) and comprises a display for a technician performing the ultrasound exam. In contrast, at least a portion of the second electronic device may be remote from the wireless ultrasound probe, at least in some embodiments. Thus, establishing the wireless network may include establishing a first, lower bandwidth wireless connection between the wireless ultrasound probe and the first electronic device via the first frequency band and establishing a second, higher bandwidth wireless connection between the wireless ultrasound probe and the second electronic device via the second frequency band.

The ultrasound exam may be performed responsive to establishing the first wireless connection between the wireless ultrasound probe and the first electronic device. As described above with respect to method 400, in some embodiments, operation of the wireless ultrasound probe may be adjusted in response to the second frequency band being unavailable for establishing the second wireless connection in order to reduce power consumption by the wireless ultrasound probe.

Therefore, at 504, the method 500 includes determining if the second frequency band is available. For example, the wireless ultrasound probe may attempt to establish the second wireless connection with the second electronic device (or vice versa) over the second frequency band and may determine that the second frequency band is unavailable in response to the second wireless connection not being established within a pre-determined, non-zero threshold duration. Additionally or alternatively, the wireless ultrasound probe may repeatedly attempt to establish the second wireless connection to the second electronic device and determine that the second frequency band is unavailable in response to reaching a pre-determined, non-zero threshold number of consecutive attempts without establishing the second wireless connection. Additionally or alternatively, in some embodiments, the second frequency band may be selectively available in response to a request received via a user interface (e.g., the user interface 115 of FIG. 1), such as described above at 404.

If the second frequency band is available (e.g., there is an active connection between the wireless ultrasound probe and the second electronic device via the second frequency band), the method 500 proceeds to 506 and includes operating the wireless ultrasound probe in a first acquisition mode to acquire ultrasound data. The first acquisition mode, used when both the first wireless connection and the second wireless connection are active, may be a higher power consumption mode compared with a second acquisition mode that may be used when the second frequency band is not available, such as described above at 406.

At 508, the method 500 includes transmitting a larger dataset of the acquired ultrasound data from the wireless ultrasound probe to the second electronic device via the second frequency band. The larger dataset may include substantially all of the data acquired while operating the probe in the first acquisition mode, including a larger field of view and every transmit line acquired, at least in some embodiments. Further, the larger dataset may undergo additional processing at the wireless ultrasound probe and error correction in the wireless channel compared with a smaller dataset that will be further described below (e.g., at 520). Additional details regarding transmitting the larger dataset via the larger bandwidth second wireless connection are described above at 408.

At 510, the method 500 includes generating higher resolution image(s) from the larger dataset at the second electronic device. For example, the processor of the second electronic device may process ultrasound signals in the larger dataset to generate slices or frames of ultrasound information (e.g., ultrasound images). Additionally or alternatively, the larger dataset may include beamformed ultrasound images that are generated at the wireless ultrasound probe and transferred to the second electronic device for further processing, display, and/or storage. As explained above at 410, in some examples, at least a portion of the higher resolution image(s) may be generated after all of the data is acquired for the ultrasound exam. In still another example, some or all of the higher resolution image(s) may be generated in response to receiving a user request for diagnostic images.

At 512, the method 500 optionally includes displaying the higher resolution image(s) responsive to a user request. As one example, a diagnosing clinician may select one or more of the high resolution image(s) for display at a display device that is remote from the wireless ultrasound probe during or after the ultrasound exam. Thus, the higher resolution image(s) may be processed, displayed, and/or saved, but are not be displayed to the operator of the wireless ultrasound probe in real-time during the ultrasound exam.

At 520, the method 500 includes transmitting the smaller dataset of the acquired ultrasound data from the wireless ultrasound probe to the first electronic device via the first frequency band in real-time. The smaller dataset comprises a subset of the larger dataset, as explained above at 420. The smaller dataset may be transmitted from the probe to the first electronic device via the first wireless connection in real-time, as the ultrasound data is acquired. The smaller dataset may include beamformed ultrasound images that are generated at the wireless ultrasound probe from a smaller amount of acquired data than the larger dataset, for example.

At 522, the method 500 includes generating the lower resolution image(s) from the smaller dataset at the first electronic device in real-time. The lower resolution image(s) may be generated in a similar manner to that described above at 410 for the higher resolution images. However, because less image information is contained in the smaller dataset compared to the larger dataset, the lower resolution images may have fewer pixels per inch, resulting in less image detail. Further, the lower image resolution image(s) may be generated in real-time, substantially at the time of data acquisition and transmission to the first electronic device.

At 524, the method 500 includes displaying the lower resolution image(s) at the first electronic device in real-time. For example, each lower resolution image may be displayed at the first electronic device as it is generated. The first electronic device may comprise a built-in display, for example, such as a touchscreen of a tablet or smartphone. The method 500 may then end. In this way, the lower resolution images(s) may be displayed to the operator in real-time via data transfer using the faster but smaller capacity first frequency band. As a result, real-time guidance feedback may be provided for the ultrasound exam that may not include sufficient detail for making a diagnosis. Further, by transferring the larger dataset via the slower but larger capacity second frequency band, higher resolution image(s) may be generated and displayed to the diagnosing clinician without delaying the real-time feedback provided to the operator during the ultrasound exam.

Returning to 504, if the second frequency band is not available (e.g., there is not an active connection between the wireless ultrasound probe and the second electronic device via the second frequency band), the method 500 proceeds to 514 and includes operating the wireless ultrasound probe in a second acquisition mode to acquire the ultrasound data. The second acquisition mode used when the second frequency band is unavailable may be a lower power consumption mode compared with the first acquisition mode described above at 506. Operating the wireless ultrasound probe in the second acquisition mode is described above with respect to 414.

At 516, the method 500 includes storing the larger dataset of the acquired ultrasound data in the probe buffer memory. Because the second frequency band is unavailable and the wireless ultrasound probe is disconnected from the second electronic device, the larger dataset is stored locally on the probe until the second frequency band becomes available. Further, by reducing the processing of the acquired ultrasound data at the probe, more probe memory may be available to store the larger dataset.

At 518, the method 500 includes again determining if the second frequency band is available, such as described above at 504. If the second frequency band remains unavailable, the method 500 may proceed to 520 to transmit the smaller dataset of the acquired ultrasound data from the wireless ultrasound probe to the first electronic device via the first frequency band in real-time, such as described above. The larger dataset may thus remain stored in the buffer memory of the probe. In response to the second frequency band becoming available, the method 500 proceeds to 508 to transfer the larger dataset of the acquired ultrasound data, including the data stored in the probe memory, to the second electronic device. Thus, operating in the second acquisition mode may include transmitting the larger dataset to the second electronic device in response to the second frequency band becoming available. Further, the probe may be transitioned to operating in the first acquisition mode, at least in some embodiments. It may be understood that if the second frequency band becomes unavailable at any point while operating in the first acquisition mode, the wireless ultrasound probe may be transitioned to operating in the second acquisition mode.

In this way, the lower resolution images(s) may be displayed to the operator in real-time even while the second frequency band is unavailable. As a result, the ultrasound exam may continue uninterrupted. Further, whether operated in the first acquisition mode or the second acquisition mode, a larger dataset of ultrasound data may be acquired that is sufficient to generate higher resolution, diagnostic-quality ultrasound images. By reducing power consumption when the second frequency band is unavailable for transmitting larger datasets and larger, more processed data, a battery life of the wireless ultrasound probe may be extended. As a result, there may be reduced downtime due to charging and a reduced occurrence of switching probes during the ultrasound exam due to battery drain.

FIGS. 6A and 6B show example transmit patterns for forming ultrasound images of different image quality, such as according to the methods of FIG. 3 or 4. In particular, FIG. 6A shows a larger, full dataset 600 of transmit lines 602, corresponding to all of the transmit lines acquired for an image frame by a wireless hand-held probe assembly (e.g., the ultrasound probe 204 of FIG. 2). The full dataset 600 may be transmitted from the wireless hand-held probe assembly to a hub (e.g., the hub 218 of FIG. 2) or another image processing device (e.g., the second electronic device 328 of FIG. 3) via a higher bandwidth wireless connection. The hub or image processing device may process the full dataset 600 to generate a higher resolution image 606. The higher resolution image 606 may be output to a display 608, which may be a display viewed by a diagnosing clinician.

In contrast, FIG. 6B shows a smaller, partial dataset 601 that includes a portion of the transmit lines 602 of the full dataset 600 of FIG. 6A. Dashed transmit lines 604 represent skipped lines that are not included in the partial dataset 601. The partial dataset 601 may be transmitted to the hub or an electronic device (e.g., the first electronic device 326 of FIG. 3) used by an operator of the wireless ultrasound probe via a lower bandwidth wireless connection in real-time, and the hub or electronic device may process the partial dataset 601 in real-time to generate a lower resolution image 610. The lower resolution image 610 may be output to a display 612 in real-time. The display 612 may be a display viewed by the operator of the wireless ultrasound probe.

As elaborated above with respect to FIGS. 2 and 3, the higher bandwidth wireless connection may enable the transfer of the larger amount of data in the full dataset 600. However, the higher bandwidth wireless connection has higher latency than the lower bandwidth wireless connection. Thus, by transferring the smaller, partial dataset 601 via the smaller bandwidth but lower latency wireless connection, the lower resolution image 610 may be generated and displayed to the operator in real-time.

In this way, an operator performing an ultrasound exam with a wireless probe may receive real-time guidance feedback via lower quality real-time images while sufficient data is acquired for generating higher quality diagnostic images. Because the diagnostic images are not used for real-time guidance, the conflicting desires for fast wireless data transfer for the real-time images and high bandwidth wireless data transfer for the diagnostic images may both be achieved via a virtual network that has two different frequency bands of differing capacities and latencies. Further, a single dataset may be acquired, with a portion of the single dataset used to generate the real-time images and all (or a larger portion) of the single dataset used to generate the diagnostic images.

Further, when a higher bandwidth wireless connection used for transferring all of the single dataset is unavailable, the ultrasound exam may continue uninterrupted. Further, power consumption by the probe may be reduced when the higher bandwidth wireless connection is unavailable, thus increasing a battery life of the wireless probe. As a result, there may be reduced wireless probe downtime and increased ultrasound exam throughput.

A technical effect of reducing an amount of data obtained, processed, and/or transferred by a wireless ultrasound probe configured to connect to one or more electronic devices via both a lower bandwidth wireless connection and a higher bandwidth wireless connection when the higher bandwidth wireless connection is unavailable is that power consumption by the wireless ultrasound probe may be reduced.

The disclosure also provides support for a method, comprising: receiving ultrasound signals of a region of interest with a wireless hand-held probe assembly, generating a plurality of received digital signals based on the received ultrasound signals within the wireless hand-held probe assembly, generating each of a larger dataset and a smaller dataset from the plurality of received digital signals, transmitting the smaller dataset from the wireless hand-held probe assembly to a hub via a lower bandwidth wireless connection, transmitting the larger dataset from the wireless hand-held probe assembly to the hub via a higher bandwidth wireless connection, generating each of a low resolution image from the smaller dataset and a high resolution image from the larger dataset at the hub, and transmitting the low resolution image from the hub to a first display and the high resolution image from the hub to an electronic device. In a first example of the method, one or both of the larger dataset and the smaller dataset include beamformed ultrasound images generated at the wireless hand-held probe assembly before being transmitted to the hub. In a second example of the method, optionally including the first example, the first display is viewable by an operator of the wireless hand-held probe assembly, and wherein transmitting the low resolution image from the hub to the first display occurs in real-time, as the ultrasound signals are received via the wireless hand-held probe assembly. In a third example of the method, optionally including one or both of the first and second examples, the electronic device comprises one or more of a second display device viewable by a diagnosing clinician, a picture archiving and communications system, and a computing device, and wherein each of transmitting the larger dataset from the wireless hand-held probe assembly to the hub via the higher bandwidth wireless connection, generating the high resolution image from the larger dataset at the hub, and transmitting the high resolution image from the hub to the electronic device is slower than real-time. In a fourth example of the method, optionally including one or more or each of the first through third examples, the method further comprises: operating the wireless hand-held probe assembly in a first acquisition mode for receiving the ultrasound signals in response to the wireless hand-held probe assembly and the hub being actively connected via the higher bandwidth wireless connection, and operating the wireless hand-held probe assembly in a second acquisition mode for receiving the ultrasound signals in response to the wireless hand-held probe assembly and the hub not being actively connected via the higher bandwidth wireless connection. In a fifth example of the method, optionally including one or more or each of the first through fourth examples, operating the wireless hand-held probe assembly in the first acquisition mode comprises at least one of acquiring more transmit lines, acquiring the ultrasound signals at a higher pulse repetition frequency, acquiring the ultrasound signals at a higher frame rate, acquiring the ultrasound signals from a larger region of interest, and performing more data processing on the plurality of received digital signals via a processor of the wireless hand-held probe assembly than when the wireless hand-held probe assembly is operated in the second acquisition mode. In a sixth example of the method, optionally including one or more or each of the first through fifth examples, operating the wireless hand-held probe assembly in the second acquisition mode comprises storing the larger dataset in a memory of the wireless hand-held probe assembly. In a seventh example of the method, optionally including one or more or each of the first through sixth examples, the method further comprises: selectively establishing the higher bandwidth wireless connection in response to a user request, and wherein transmitting the larger dataset from the wireless hand-held probe assembly to the hub via the higher bandwidth wireless connection is in response to establishing the higher bandwidth wireless connection. In an eighth example of the method, optionally including one or more or each of the first through seventh examples, the first display is at a same location as the wireless hand-held probe assembly, and wherein the electronic device is at the same location or remote from the wireless hand-held probe assembly. In a ninth example of the method, optionally including one or more or each of the first through eighth examples, the first display is included in an augmented reality headset worn by an operator of the wireless hand-held probe assembly. In a tenth example of the method, optionally including one or more or each of the first through ninth examples, the lower bandwidth wireless connection uses a first frequency band of 7 gigahertz or less, and the higher bandwidth wireless connection uses a second frequency band of 60 gigahertz or greater.

The disclosure also provides support for a method, comprising: establishing a first wireless connection between a wireless hand-held probe assembly and an image processing hub, transmitting a first dataset of data acquired by the wireless hand-held probe assembly to the image processing hub in real-time via the first wireless connection, generating lower resolution images from the first dataset at the image processing hub in real-time, transmitting the lower resolution images from the image processing hub to a display device of an operator of the wireless hand-held probe assembly in real-time, establishing a second wireless connection between the wireless hand-held probe assembly and the image processing hub, the second wireless connection using a different bandwidth than the first wireless connection, transmitting a second dataset of the data acquired by the wireless hand-held probe assembly to the image processing hub via the second wireless connection, and generating higher resolution images at the image processing hub from the second dataset, wherein the second dataset comprises some or all of the first dataset and additional data acquired by the wireless hand-held probe assembly that is not included in the first dataset. In a first example of the method, the first wireless connection uses a first frequency band that has at least one of a lower frequency, a lower bandwidth, and a lower latency than a second frequency band used for the second wireless connection. In a second example of the method, optionally including the first example, establishing the first wireless connection is in response to acquiring data via the wireless hand-held probe assembly, and wherein establishing the second wireless connection is in response to a user request. In a third example of the method, optionally including one or both of the first and second examples, transmitting the second dataset is in response to establishing the second wireless connection. In a fourth example of the method, optionally including one or more or each of the first through third examples, the method further comprises: outputting the higher resolution images to one or more of a second display device, a picture archiving and communications system, a remote computing device, and a remote display device.

The disclosure also provides support for a system, comprising: one or more memories storing instructions, and at least one processor communicably coupled to the one or more memories and, when executing the instructions, configured to: establish a first wireless connection between an ultrasound probe and a first electronic device via a lower bandwidth connection in response to commencing an ultrasound exam, transmit a smaller dataset of ultrasound data acquired by the ultrasound probe from the ultrasound probe to the first electronic device, as the ultrasound data is acquired, via the first wireless connection, establish a second wireless connection between the ultrasound probe and one of the first electronic device and a second electronic device via a higher bandwidth connection, transmit a larger dataset of the ultrasound data from the ultrasound probe to the one of the first electronic device and the second electronic device via the second wireless connection, generate a lower resolution image from the smaller dataset at the first electronic device and output the lower resolution image to a first display device in real-time, and generate a higher resolution image from the larger dataset at the one of the first electronic device and the second electronic device. In a first example of the system, the first electronic device is an image processing hub, and the at least one processor, when executing the instructions, is further configured to: establish the second wireless connection between the ultrasound probe and the first electronic device via the higher bandwidth connection, transmit the larger dataset of the ultrasound data from the ultrasound probe to the first electronic device via the second wireless connection, generate the higher resolution image from the larger dataset at the first electronic device, and establish a third wireless connection between the first electronic device and the first display device via the lower bandwidth connection, the first display device local to the ultrasound probe. In a second example of the system, optionally including the first example, the first display device is included in the first electronic device, the first electronic device is local to the ultrasound probe, and the at least one processor, when executing the instructions, is further configured to: transmit the larger dataset of the ultrasound data from the ultrasound probe to the second electronic device via the second wireless connection, generate the higher resolution image from the larger dataset at the second electronic device, store the higher resolution image at the second electronic device, and output the higher resolution image from the second electronic device to a second display device that is remote from the ultrasound probe in response to a user request to view the higher resolution image. In a third example of the system, optionally including one or both of the first and second examples, the instructions that cause the at least one processor to establish the second wireless connection between the ultrasound probe and the one of the first electronic device and the second electronic device via the higher bandwidth connection is in response to receiving a user request, wherein the lower bandwidth connection uses a lower frequency band, and wherein the higher bandwidth connection uses a higher frequency band.

In another representation, a method comprises: receiving ultrasound signals of a region of interest with a hand-held probe assembly; generating a plurality of received digital signals based on the ultrasound signals within the hand-held probe assembly; generating each of a larger dataset and a smaller dataset from the plurality of received digital signals; transmitting the smaller dataset of the acquired data to a first electronic device via a lower bandwidth wireless connection; transmitting the larger dataset of the acquired data to a second electronic device via a higher bandwidth wireless connection; generating a low resolution image from the smaller dataset at the first electronic device; generating a high resolution image from the larger dataset at the second electronic device; and displaying the low resolution image in real-time. In a first example of the method, the first electronic device is one of a personal digital assistant, a smartphone, a tablet computer, and a laptop computer. In a second example of the method, optionally including the first, the second electronic device stores the generated high resolution image and outputs the generated high resolution image to a display device in response to a user request.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
receiving a single full dataset of ultrasound signals for a region of interest with a wireless hand-held probe assembly;
generating a plurality of received digital signals based on the single full dataset of received ultrasound signals within the wireless hand-held probe assembly;
generating each of a larger dataset and a smaller dataset from the plurality of received digital signals that are based on the single full dataset;
transmitting the smaller dataset from the wireless hand-held probe assembly to a hub via a lower bandwidth wireless connection;
transmitting the larger dataset from the wireless hand-held probe assembly to the hub via a higher bandwidth wireless connection, wherein the higher bandwidth wireless connection is a separate connection from the lower bandwidth wireless connection;
generating each of a low resolution image from the smaller dataset and a high resolution image from the larger dataset at the hub; and
transmitting the low resolution image from the hub to a first display and the high resolution image from the hub to an electronic device.

2. The method of claim 1, wherein one or both of the larger dataset and the smaller dataset include beamformed ultrasound images generated at the wireless hand-held probe assembly before being transmitted to the hub.

3. The method of claim 1, wherein the first display is configured to be viewable by an operator of the wireless hand-held probe assembly, and wherein transmitting the low resolution image from the hub to the first display occurs in real-time, as the ultrasound signals are received via the wireless hand-held probe assembly.

4. The method of claim 1, wherein the electronic device comprises one or more of a second display device, a picture archiving and communications system, and a computing device, wherein the second display device is configured to be viewable by a diagnosing clinician, and wherein each of transmitting the larger dataset from the wireless hand-held probe assembly to the hub via the higher bandwidth wireless connection, generating the high resolution image from the larger dataset at the hub, and transmitting the high resolution image from the hub to the electronic device is slower than real-time.

5. The method of claim 1, further comprising:
operating the wireless hand-held probe assembly in a first acquisition mode for receiving the ultrasound signals in response to the wireless hand-held probe assembly and the hub being actively connected via the higher bandwidth wireless connection; and
operating the wireless hand-held probe assembly in a second acquisition mode for receiving the ultrasound signals in response to the wireless hand-held probe assembly and the hub not being actively connected via the higher bandwidth wireless connection.

6. The method of claim 5, wherein operating the wireless hand-held probe assembly in the first acquisition mode comprises at least one of acquiring more transmit lines, acquiring the ultrasound signals at a higher pulse repetition frequency, acquiring the ultrasound signals at a higher frame rate, acquiring the ultrasound signals from a larger region of interest, and performing more data processing on the plurality of received digital signals via a processor of the wireless hand-held probe assembly than when the wireless hand-held probe assembly is operated in the second acquisition mode.

7. The method of claim 5, wherein operating the wireless hand-held probe assembly in the second acquisition mode comprises storing the larger dataset in a memory of the wireless hand-held probe assembly.

8. The method of claim 1, further comprising:
selectively establishing the higher bandwidth wireless connection in response to a user request, and wherein transmitting the larger dataset from the wireless hand-held probe assembly to the hub via the higher bandwidth wireless connection is in response to establishing the higher bandwidth wireless connection.

9. The method of claim 1, wherein the first display is at a same location as the wireless hand-held probe assembly, and wherein the electronic device is at the same location or remote from the wireless hand-held probe assembly.

10. The method of claim 1, wherein the first display is included in an augmented reality headset worn by an operator of the wireless hand-held probe assembly.

11. The method of claim 1, wherein:
the lower bandwidth wireless connection uses a first frequency band of 7 gigahertz or less; and
the higher bandwidth wireless connection uses a second frequency band of gigahertz or greater.

12. A method, comprising:
acquiring a single full dataset of ultrasound signals for a region of interest with a wireless hand-held probe assembly;
establishing a first wireless connection between the wireless hand-held probe assembly and an image processing hub;
transmitting a first dataset from the single full dataset acquired by the wireless hand-held probe assembly to the image processing hub in real-time via the first wireless connection;
generating lower resolution images from the first dataset at the image processing hub in real-time;
transmitting the lower resolution images from the image processing hub to a display device of an operator of the wireless hand-held probe assembly in real-time;
establishing a second wireless connection between the wireless hand-held probe assembly and the image processing hub, the second wireless connection using a different bandwidth than the first wireless connection, wherein the first wireless connection is a separate connection from the second wireless connection;
transmitting a second dataset from the single full dataset acquired by the wireless hand-held probe assembly to the image processing hub via the second wireless connection; and
generating higher resolution images at the image processing hub from the second dataset, wherein the second dataset comprises some or all of the first dataset and additional data acquired by the wireless hand-held probe assembly that is not included in the first dataset, wherein the data used for the first dataset and the second dataset is based on the single full dataset of ultrasound signals acquired by the wireless hand-held probe assembly.

13. The method of claim 12, wherein the first wireless connection uses a first frequency band that has at least one of a lower frequency, a lower bandwidth, and a lower latency than a second frequency band used for the second wireless connection, and wherein transmission of both the first dataset and the second dataset is carried out in a same acquisition mode.

14. The method of claim 12, wherein establishing the first wireless connection is in response to acquiring data via the wireless hand-held probe assembly, and wherein establishing the second wireless connection is in response to a user request.

15. The method of claim 14, wherein transmitting the second dataset is in response to establishing the second wireless connection.

16. The method of claim 12, further comprising:
outputting the higher resolution images to one or more of a second display device, a picture archiving and communications system, a remote computing device, and a remote display device.

17. A system, comprising:
one or more memories storing instructions; and
at least one processor communicably coupled to the one or more memories and, when executing the instructions, configured to:
in a first acquisition mode,
establish a first wireless connection between an ultrasound probe and a first electronic device via a lower bandwidth connection in response to commencing an ultrasound exam;
transmit a smaller dataset of ultrasound data based on a single full dataset of ultrasound signals acquired by the ultrasound probe from the ultrasound probe to the first electronic device, as the ultrasound data is acquired, via the first wireless connection;
establish a second wireless connection between the ultrasound probe and the first electronic device, or between the ultrasound probe and a second electronic device, via a higher bandwidth connection;
transmit a larger dataset based on the single full dataset of ultrasound signals acquired from the ultrasound probe to the one of the first electronic device and the second electronic device via the second wireless connection, wherein the first wireless connection is a separate connection from the second wireless connection;
generate a lower resolution image from the smaller dataset at the first electronic device and output the lower resolution image to a first display device in real-time; and
generate a higher resolution image from the larger dataset at the one of the first electronic device and the second electronic device.

18. The system of claim 17, wherein the first electronic device is an image processing hub, and the at least one processor, when executing the instructions, is further configured to:
establish the second wireless connection between the ultrasound probe and the first electronic device via the higher bandwidth connection;
transmit the larger dataset of the ultrasound data from the ultrasound probe to the first electronic device via the second wireless connection;
generate the higher resolution image from the larger dataset at the first electronic device; and
establish a third wireless connection between the first electronic device and the first display device via the lower bandwidth connection, the first display device local to the ultrasound probe.

19. The system of claim 17, wherein the first display device is included in the first electronic device, the first electronic device is local to the ultrasound probe, and the at least one processor, when executing the instructions, is further configured to:
transmit the larger dataset of the ultrasound data from the ultrasound probe to the second electronic device via the second wireless connection;
generate the higher resolution image from the larger dataset at the second electronic device;
store the higher resolution image at the second electronic device; and
output the higher resolution image from the second electronic device to a second display device that is remote from the ultrasound probe in response to a user request to view the higher resolution image.

20. The system of claim 17, wherein the instructions that cause the at least one processor to establish the second wireless connection between the ultrasound probe and the one of the first electronic device and the second electronic device via the higher bandwidth connection is in response to receiving a user request, wherein the lower bandwidth connection uses a lower frequency band, and wherein the higher bandwidth connection uses a higher frequency band.

\* \* \* \* \*